US009415167B2

(12) United States Patent
Hayes et al.

(10) Patent No.: US 9,415,167 B2
(45) Date of Patent: Aug. 16, 2016

(54) INFRARED SKIN DETECTION SENSOR

(75) Inventors: Matthew Hayes, Cambridge (GB); Paul David Ryder, Suffolk (GB); Alain Schmidlin, Marckolsheim (FR); Nicholas Troop, Cambridge (GB)

(73) Assignee: Novartis AG, Basel (CH)

( * ) Notice: Subject to any disclaimer, the term of this patent is extended or adjusted under 35 U.S.C. 154(b) by 278 days.

(21) Appl. No.: 14/006,124

(22) PCT Filed: Mar. 20, 2012

(86) PCT No.: PCT/EP2012/054927
§ 371 (c)(1),
(2), (4) Date: Sep. 19, 2013

(87) PCT Pub. No.: WO2012/126915
PCT Pub. Date: Sep. 27, 2012

(65) Prior Publication Data
US 2014/0018768 A1  Jan. 16, 2014

Related U.S. Application Data

(60) Provisional application No. 61/466,193, filed on Mar. 22, 2011.

(51) Int. Cl.
*G01C 3/08* (2006.01)
*A61M 5/31* (2006.01)
(Continued)

(52) U.S. Cl.
CPC . *A61M 5/31* (2013.01); *A61M 5/20* (2013.01); *G01N 21/4738* (2013.01); *G01N 21/4795* (2013.01); *A61M 5/427* (2013.01); *A61M2005/206* (2013.01); *A61M 2005/2013* (2013.01); *G01N 21/35* (2013.01)

(58) Field of Classification Search
CPC ...... A61M 5/20; A61M 5/31; G01N 21/4738; G01N 21/4795
See application file for complete search history.

(56) References Cited

U.S. PATENT DOCUMENTS 7,884,933 B1 * 2/2011 Kashyap ............. G01N 21/474
356/338

(Continued)

FOREIGN PATENT DOCUMENTS

EP          0710832 B1   1/2002
WO       2009037432 A1   3/2009

OTHER PUBLICATIONS

International Search Report, PCT/EP2012/054927 (Jul. 4, 2012).

*Primary Examiner* — Luke Ratcliffe
*Assistant Examiner* — Samantha K Abraham
(74) *Attorney, Agent, or Firm* — Michael Mazza

(57) ABSTRACT

The invention relates to an electronic sensor for detecting skin, the sensor comprising processor, an EM source, a baffle, a first EM detector and a second EM detector, the sensor arranged such that the EM source is located on a first side of the baffle and the first and second EM detectors are arranged on a second opposite side of the baffle at first and second distances from the EM source respectively, the first distance being less than the second distance, the processor configured to cause the source to emit EM radiation and to receive first and second signals from the first and second EM detectors respectively, the signals being indicative of the intensity of EM radiation detected by the sensor, the processor being further configured to process the first and second signals and thereby generate a skin signal which is indicative of whether the sensor has detected skin.

10 Claims, 3 Drawing Sheets

(51) Int. Cl.
*A61M 5/20* (2006.01)
*G01N 21/47* (2006.01)
*A61M 5/42* (2006.01)
*G01N 21/35* (2014.01)

(56) References Cited

U.S. PATENT DOCUMENTS

| | | | | |
|---|---|---|---|---|
| 2002/0084417 A1* | 7/2002 | Khalil | ................ | A61B 5/14532 250/341.8 |
| 2005/0260745 A1* | 11/2005 | Domansky | ............. | C12M 29/10 435/294.1 |
| 2007/0253833 A1* | 11/2007 | Hanlon | ............. | A61M 5/14232 417/63 |
| 2009/0239051 A1* | 9/2009 | Fukuda | ................ | C08L 101/00 428/220 |
| 2012/0116212 A1* | 5/2012 | Bral | ........................ | A61N 1/08 600/424 |

* cited by examiner

INFRARED SKIN DETECTION SENSOR

The present invention relates to a sensor for detecting skin and is particularly intended for use in an autoinjector, particularly a reconstituting autoinjector.

Some medicaments are administered to a patient by injecting a liquid formulation of the medicament into the patient. This is typically performed using a needle coupled to a syringe. In some cases the liquid formulation is not stable in the liquid form and is supplied as a dried medicament and a reconstituting liquid. Prior to injection the reconstituting liquid is added to the dried medicament to create the injectable liquid formulation. It is known to use an autoinjector to automate at least part of the process of injecting a patient, such as a human or animal. Automation of the injection step is particularly useful where a consistent depth and/or volume of injection is desirable.

It may be desirable to avoid unwanted activation of an automatic injection operation. It may be desirable for injection to occur into, or through, the skin of a patient and a means of detecting proximity to an object to be injected has been included in some autoinjectors. In some cases a mechanical probe has been used to detect a surface to be injected, in other cases a capacitive sensor has been used to detect contact with skin prior to injection.

The present invention provides an electronic sensor for detecting skin, the sensor comprising processor, an EM source, a baffle, a first EM detector and a second EM detector, the sensor arranged such that the EM source is located on a first side of the baffle and the first and second EM detectors are arranged on a second, opposite, side of the baffle at first and second distances from the EM source respectively, the first distance being less than the second distance, the processor configured to cause the source to emit EM radiation and to receive first and second signals from the first and second EM detectors respectively, the signals being indicative of the intensity of EM radiation detected by the sensor, the processor being further configured to process the first and second signals and thereby generate a skin signal which is indicative of whether the sensor has detected skin.

When light, particularly infrared (IR) light, is shone into the surface of a highly scattering material (such as a body tissue like fat or muscle, or a combination of the two), the photons are both absorbed and scattered in multiple directions in a process that can be modelled statistically. The result of this scattering is that a bright path (high relative average photon density) will exist within the material, and that the light will be detected at the material surface some distance from the source. The profile of light intensity at the material surface as a function of distance from the source is characteristic of the scattering material. Providing two detectors at different distances from the source means that the difference between intensity of light at each of the detectors is indicative of the characteristic of the material and this difference can therefore be used to determine whether the material into which the light is being shone has the light scattering characteristic of a body tissue into which an injection can occur.

The EM source illuminates the surface of the material to be tested with electromagnetic (EM) radiation, while the two detectors measure the intensity of EM radiation emerging from the material in two positions at different distances from the source. The EM source may emit any suitable EM radiation. It may emit EM radiation between infrared and ultraviolet wavelengths. It may emit radiation only in the infrared spectrum between wavelengths of about 0.7 micrometers and about 300 micrometers.

The sensor is intended to test for the presence of tissue into which an injection can be made. A positive reading from the sensor can be taken as indicator that the sensor is in close proximity to skin. The first sensor may be positioned at the expected bright-spot for suitable tissue and the second sensor may be positioned adjacent to it as this will provide the biggest difference in signal strengths between the first and second sensors. Although the transmission of the EM radiation through the tissue is an important characteristic living tissue is not of a consistent character and the characteristic will vary at different sites around the body. For example muscle and fat will have a different scattering characteristic. In order for the sensor to produce a positive skin signal the EM radiation emitted from the source must be detected by the sensors after it has passed through a medium. As mentioned above, the scattering characteristic of tissues varies so when the sensor is in close proximity or contact with a tissue with a scattering characteristic as determined by the processing of the two signals from the detectors that matches a scattering characteristic determined for tissue into which an injection can occur the sensor is able to generate a skin signal.

It should be understood that the term skin in this document is intended to refer to tissue into which an injection can occur, for example fat, muscle or other body tissue and not simply human or animal skin. Since the human or animal body is typically substantially covered in skin it can usually be assumed that if the sensor detects such tissue, it is in contact with, or close proximity to, skin.

Providing a small source can facilitate the determination of the characteristic so the EM source may be substantially a point source, or a source small enough to be considered substantially equivalent to one. This could be achieved by providing a plate opaque to the emitted EM radiation through which there is a pin-hole between the EM source and the material to be tested. The pin hole may be less than 5 mm, less than 2.5 mm or less than 1.5 mm. The pinhole may be between about 1.5 mm and 1 mm. For these dimensions it is intended that the dimension refers to a diameter, or maximum dimension of the aperture for apertures that are not substantially circular in shape.

The baffle is intended to prevent a direct light path from the EM source to either of the detectors. The baffle may be substantially planar, curved, or a combination of the two. The baffle may substantially surround the EM source. The baffle, first EM detector and second EM detector may be arranged substantially in a straight line.

If the EM source emits IR radiation, the sensor may include a cover of IR transmitting glass. Such a cover could protect the sensor from dirt contamination or physical damage. Such a cover should cover one or more of the emitter and detectors and more than one cover may be provided.

In order to generate a skin signal which is indicative of whether the sensor has detected skin the processor may compare the first signal strength with a first threshold to determine if the signal is strong enough to indicate that the sensor is in contact, or at least close proximity, to an IR transmissive material that has an IR scattering characteristic that is indicative of being a material into which an injection can be made.

In order to generate a skin signal which is indicative of whether the sensor has detected skin the processor may compare the ratio between the first and second signals with a second threshold to determine whether the material has an IR scattering characteristic that is indicative of being a material into which an injection can be made.

The processor may also monitor the rate of change of at least one of the first and second signals and compare that rate of change with a threshold to determine whether the signals are stable as this may assist in preventing the generation of false positive skin signals.

It should be understood that the thresholds mentioned above will depend upon many factors, for example the EM radiation being used, the location of the skin to be detected, the risk of false positives or false negatives that can be tolerated. It should be possible to set suitable limits using basic trial and error methods.

The IR source may be an Infra Red LED, or any other suitable source and the IR detectors may be photodiodes capable of detecting incident IR radiation intensity, or any other suitable detector capable of generating a signal indicative of the intensity of IR light reaching the detector. In one embodiment the wavelength of EM radiation used is between 900 and 1000 nm.

The distance between the IR source and the first sensor may be between 0.1 cm and 0.6 cm, between 0.2 cm and 0.5 cm or may be substantially 0.3 cm. The difference in the distance from the EM source between the first sensor and the second sensor may be between 0.1 cm and 1 cm, between 0.2 cm and 0.7 cm or between about 0.3 cm and 0.5 cm. This distance may be the distance between the two detectors if the detectors are positioned along a substantially straight line from the source to the first detector and then the second detector. However, since the scattering within the tissue is not limited to a single line, but radiates from the source so the detectors need not be arranged along a line extending through the emitter.

The invention also provides an autoinjector comprising a liquid container, an injector, an injection contact portion, processor and a sensor adjacent the injection contact portion, the injector is arranged to inject liquid from the liquid container into a patient at the injection contact portion, the sensor being substantially as described above and the autoinjector being configured to use the injector to inject the liquid from the container into a subject only when a positive skin signal has been received from the sensor.

The autoinjector may include an ambient light sensor adjacent the sensor and the autoinjector may be configured to activate the sensor only when the ambient light sensor detects ambient light levels below a threshold level.

The autoinjector may be a reconstituting autoinjector which is capable of receiving a dry medicament product and a reconstitution liquid, automatically combining them to provide an injectable medication and subsequently automatically injecting them into a patient. There may be user steps to complete before, during or after each of the automated steps.

The invention extends to a method of generating a signal indicative of contact of an object with skin, the object being equipped with a sensor on a contact portion thereof, the sensor comprising a processor, an EM source, a baffle, a first EM detector and a second EM detector, the sensor arranged such that the EM source is located on a first side of the baffle and the first and second EM detectors are arranged on a second opposite side of the baffle at first and second distances from the EM source respectively, the first distance being less than the second distance, the method comprising the steps of:
 a) using the processor to cause the source to emit EM radiation
 b) using the first and second EM detectors to generate first and second signals respectively, the signals being indicative of the intensity of EM radiation detected by the sensor; and
 c) using the processor to process the first and second signals and thereby generate a skin signal which is indicative of whether the sensor has detected skin and therefore whether the object has contacted skin.

The object may be an autoinjector. The autoinjector may be as described above.

It should be understood that throughout this specification and in the claims that follow, unless the context requires otherwise, the word "comprise", or variations such as "comprises" or "comprising", implies the inclusion of the stated integer or step, or group of integers or steps.

The invention will now be further described, by way of example only, with reference to the following drawings in which.

Figure 1:
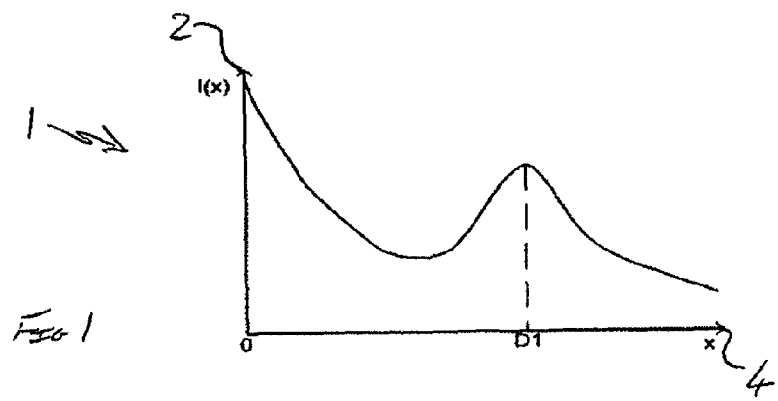
FIG. 1 shows a graph of IR light intensity against distance from a source at the surface of a material.

FIG. 1 shows a graph 1 with light intensity (I) on the vertical axis 2 and distance from a light source (x) on the horizontal axis 4. The graph 1 shows how the light intensity (I) varies as a function of distance (x) from the source. It can be seen from the graph 1 that the light intensity (I) initially falls with increasing distance from the source, but then rises to a maximum at the point D1 from the source before falling again. The distance D1 is indicative of a characteristic of the light scattering properties of a material into which the light is being shone. In this case the light is an IR light.

Figure 2:
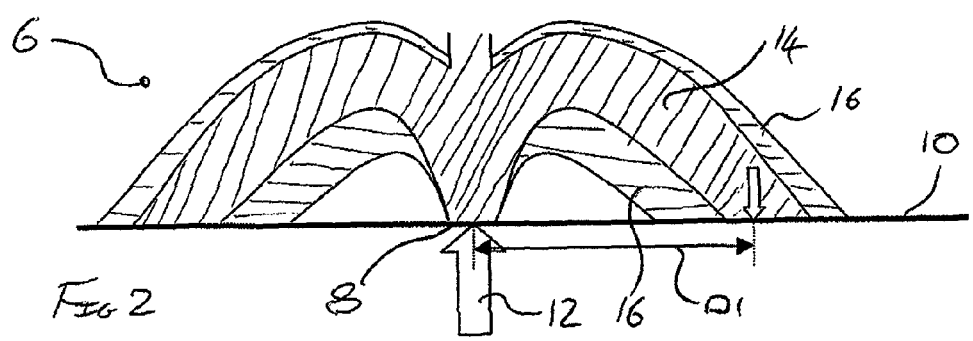
FIG. 2 shows a schematic of light intensity within a material.

FIG. 2 shows a schematic of the light intensity within a material 6 when a portion 8 of a surface 10 is illuminated with IR light 12. Due to light scattering within the material 6 a 'bright path' 14 is established within the material 6 in which the average light intensity is relatively higher than elsewhere. The bright path 14 is bounded by a lower intensity path 16. The bright path 14 curves through the material from the illuminated surface portion 8 until it reaches the surface 10 again at a point a distance D1 from the illuminated portion 8.

Figure 3:
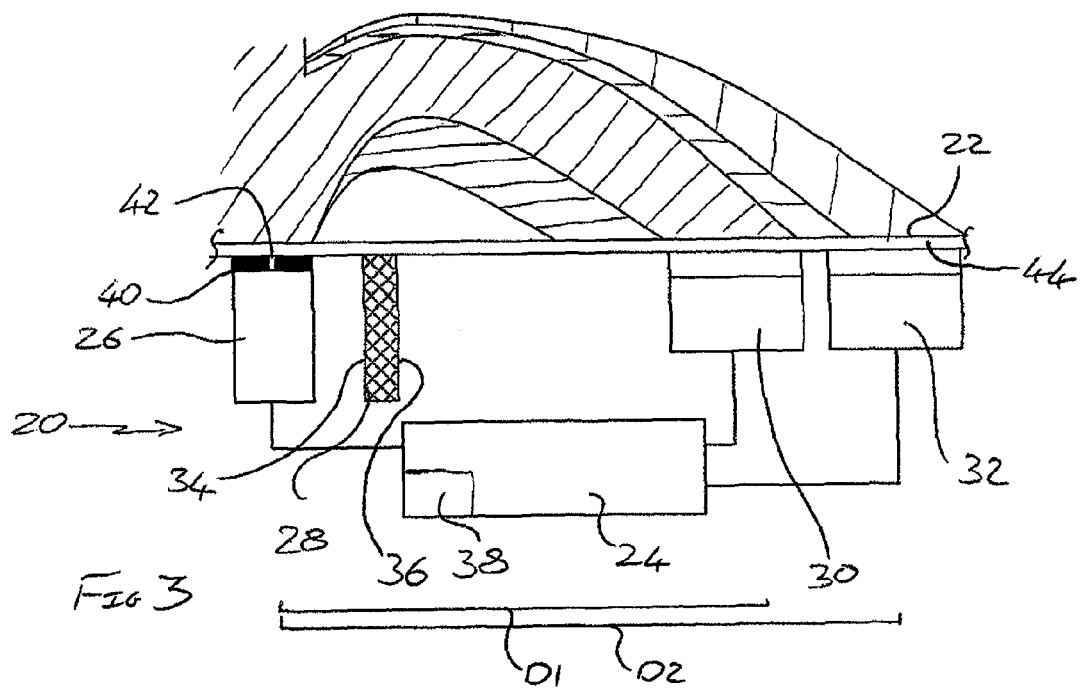
FIG. 3 shows a sensor.

FIG. 3 shows an electronic sensor 20 for detecting skin 22, the sensor 20 comprises processor 24, an IR source 26, in this case an Infra Red emitting LED, a baffle 28, a first IR detector 30 and a second IR detector 32, in this case photo diodes. The IR source 26 includes an opaque plate 40 through which there is a pinhole 42 so that the IR source projects a fine point of IR light. The diameter of the pinhole may be less than 2 mm, may be less than 1 mm or may be less than 0.5 mm. The optical power emerging through the pin hole is approximately 14 mW.

The sensor further includes a cover 44 of a material through which IR radiation can pass. The cover 44 is arranged to cover the IR source 26, baffle 28, first IR detector 30 and second IR detector 32.

The sensor 20 is arranged such that the IR source 26 is located on a first side 34 of the baffle 28 and the first and second IR detectors 30,32 are arranged on a second, opposite, side 36 of the baffle 28 at first and second distances D1,D2 from the IR source 26 respectively. The baffle 28 prevents IR light from passing directly from the IR source 26 to the detectors 30,32. The first distance D1 is less than the second distance D2. D1 is chosen to approximately equal the expected distance D1 between the IR source 26 and the point at which the bright path mentioned above reaches the surface of flesh, or other suitable body tissue, covered by skin. The IR source 24, baffle 28, first and second detectors 30,32 are arranged substantially along a straight line.

The processor 24 is configured to selectively cause the IR source 26 to emit IR radiation and to receive first and second signals S1,S2 from the first and second IR detectors 30,32 respectively. The sensor 20 further includes a power source 38 to provide power the various components. The power source 38 may be integral with the sensor, or external. The signals received are indicative of the intensity of IR radiation detected by each sensor 30,32. The processor is configured to process the first and second signals and thereby generate a skin signal which is indicative of whether the sensor has detected skin.

Figure 4:
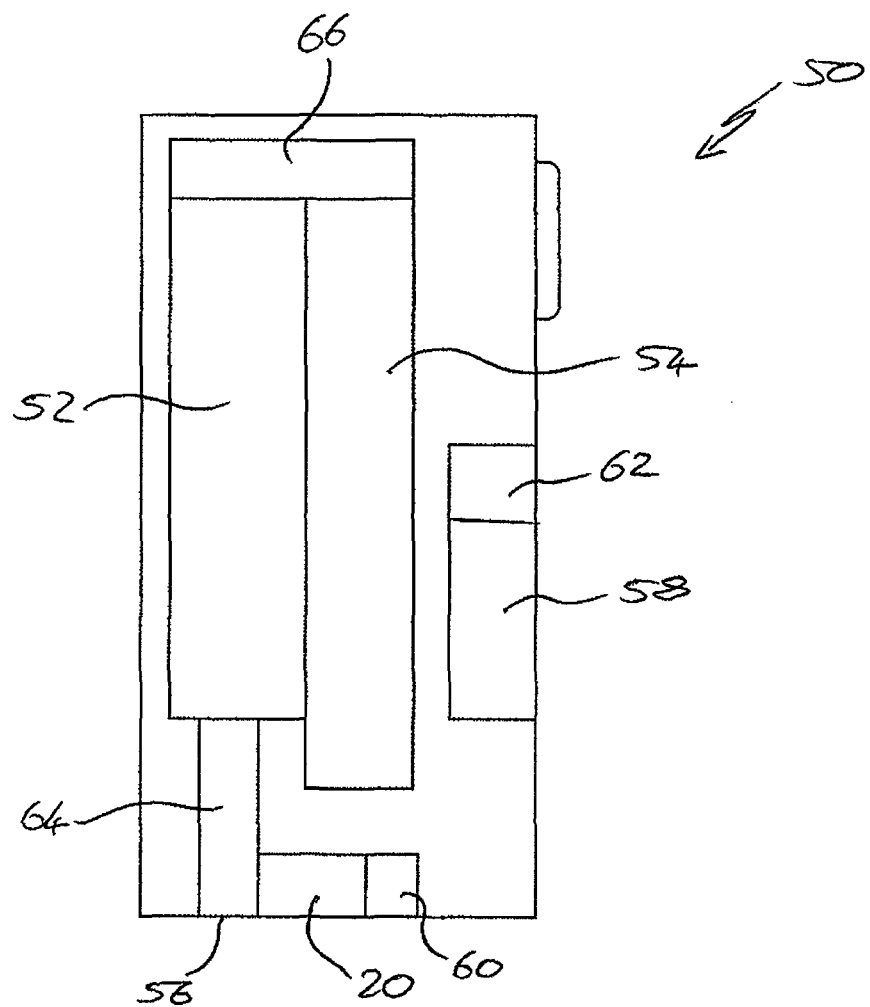
FIG. 4 shows an autoinjector comprising a sensor.

FIG. 4 shows an autoinjector 50 comprising a liquid container 52, an injector 54, an injection contact portion 56, processor 58 and a sensor 20 adjacent the injection contact portion 56. The injector 54 is arranged to inject liquid from the liquid container 52 into a patient at the site of the injection contact portion 56. The autoinjector 50 is configured to use the injector 54 to inject the liquid into a subject only when a positive skin signal has been received from the sensor 20.

The autoinjector 50 further includes an ambient light sensor 60 adjacent the sensor 20 for measuring the intensity of the ambient light. The autoinjector 50 further comprises a power source 62. It should be noted that either, both or neither the processor 58 and the power source 62 may be integral with the power source 38 and processor 24 of the sensor 20 and be located within, or external to the sensor 20.

In this case the liquid container 52 is a syringe which is coupled to a needle 64 through which liquid can be injected. The injector 54 comprises drive means 66 which can be operated to force liquid from the container 52 through the needle 64. The injector 54 is also operable to move the needle 64 out of the autoinjector 50 at the injection contact portion 56 so that, if the autoinjector 50 is located with the injection contact portion 56 against the skin of a patient, the autoinjector can inject the liquid into a patient through the needle 64.

Figure 5:
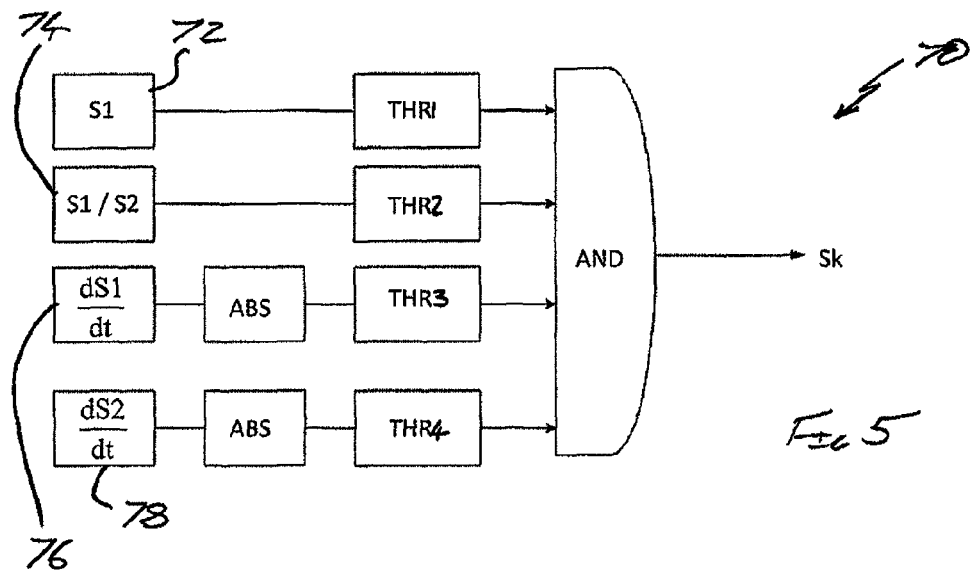
FIG. 5 shows a logic gate for use in the sensor of FIG. 3.

FIG. 5 shows a logic gate 70 suitable for use in the sensor of FIG. 3. The logic gate 70 is an AND gate with four inputs 72, 74, 76, 78. The first input 72 is the signal S1 from the first sensor 30. The signal S1 is checked against a threshold THR1 and, if S1 is greater than THR1, a positive signal is passed to the logic gate 70.

The second input 74 is the ratio of the signal S1 from the first sensor 30 divided by the signal S2 from the second sensor 32. The resulting ratio S1/S2 is checked against a threshold THR2 and, if greater than THR2, a positive signal is passed to the logic gate 70. It has been found that the ratio of S1/S2 is between about 2 and 6 when the sensor is in contact with skin. Therefore THR2 may be at least 2.

The third and fourth inputs 76,78 are respectively the derivatives of the signals S1 and S2 with respect to time. The absolute values of the derivatives are checked against thresholds THR3 and THR4 respectively and, if the derivative is below the threshold, a positive signal is passed to the logic gate 70.

If the AND Gate 70 receives a positive signal as a result of all the four inputs 72, 74, 76, 78 then a positive skin signal, Sk, is generated. If any, or all, of the four inputs 72, 74, 76, 78 results in a negative signal being passed to the logic gate 70 then a negative skin signal, Sk, is generated.

Figure 6:
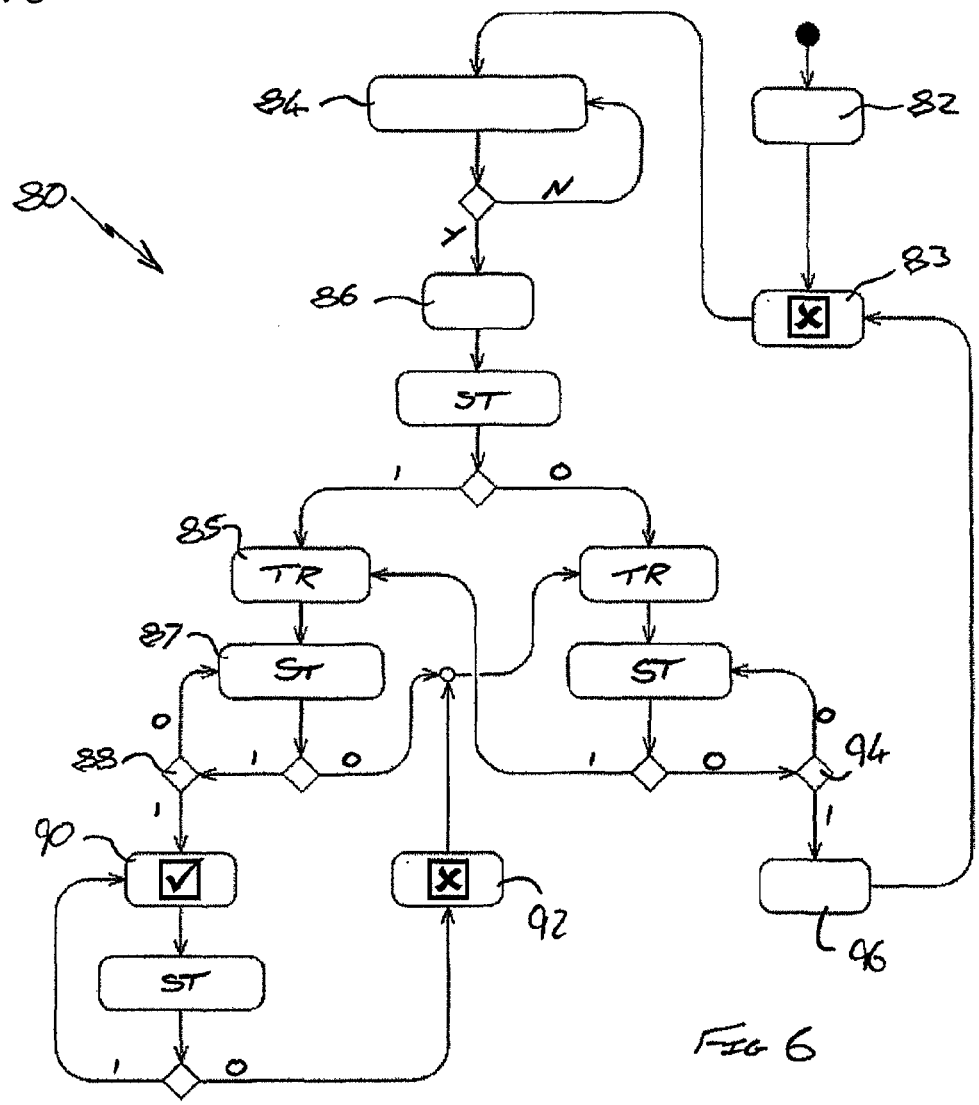
FIG. 6 shows a flowchart for operations within the autoinjector of FIG. 4.

FIG. 6 shows a flow chart 80 for operations within the autoinjector of FIG. 4. The flowchart starts with Initialisation at step 82 and begins with a negative output, X at step 83, so no injection operation occurs. The first test occurs at step 84 when the output from the ambient light sensor 60 is checked against a threshold. If above the threshold (Y) then the IR source is turned on in step 86 and a skin test (ST) conducted. The skin test is a check of the output from the skin sensor 20. A positive output from the skin sensor 20 is a 1, indicating skin has been detected, and a negative output is a 0.

In the event of a positive output a timer is reset to zero (TR) in step 85 and a further skin test (ST) carried out in step 87. In the event of another positive output the timer is checked in step 88 and, if the timer indicates a time of more than 0.2 s since the timer reset (TR) then a positive output is generated in step 90 indicating that the autoinjector can now carry out an injection cycle, or at least move on to the next operation. Following the generation of a positive output in step 90 further skin tests (ST) are conducted to ensure that a positive output is still appropriate. If the further skin test is positive then the positive output in step 90 is maintained and a loop is entered.

However, if the skin test (ST) is negative then a negative output is generated in step 92 and the flowchart returns to a point as if the skin test (ST) at step 87 had been negative. The timer is again reset (TR) and a skin test (ST) conducted. A positive output from this skin test (ST) returns the process to the timer rest of step 85. A negative output moves the process to step 94 in which the timer is checked and, if the timer indicates a time of more than 2 s since the last timer reset (TR) then a positive output is generated in step 94. A negative output from step 94 returns the process to the skin test (ST) step. A positive output in step 94 results in the IR source being powered down in step 96 and the process returning to a negative output being generated in step 83.

This flowchart results in a positive output in step 90 only if a positive skin test is positive each time it is checked for at least 0.2 s and will remain positive only for as long as the skin test results remain positive.

However if a consistent negative skin test is returned for at least 2 s then the IR source is turned off to save energy and the ambient light levels are checked in step 84 to ensure that the autoinjector is still located against a surface.

It should be understood that the flowchart described above is only a possible way in which the device could be arranged to operate and there may be additional steps, steps omitted and/or steps occurring in a different order.

It should be understood that the invention has been described above by way of example only and that modifications in detail can be made without departing from the scope of the claims.

The invention claimed is:

1. An electronic sensor for detecting skin, the sensor comprising a processor, an EM source which projects a fine point of IR light, a baffle, a first EM detector and a second EM detector, the sensor arranged such that the EM source is located on a first side of the baffle and the first and second EM detectors are arranged on a second, opposite, side of the baffle at first and second distances from the EM source respectively, the first distance being less than the second distance, the processor configured to cause the source to emit EM radiation and to receive first and second signals from the first and second EM detectors respectively, the signals being indicative of the intensity of EM radiation detected by the sensor, the processor being further configured to process the first and second signals wherein the first signal is input to a logic gate and is compared against a first threshold, and if greater, a positive signal is passed to the logic gate; said first signal is divided by said second signal, and compared to a second threshold, and if greater a positive signal is passed to the logic gate, a rate of change of each of said first and second signals is obtained and compared to a third and a fourth threshold, wherein a positive signal is passed to the logic gate if the rate of change of said first and second signals is below said third and fourth thresholds, and wherein a summation of all four positive signals generates a positive skin detection signal.

2. A sensor as claimed in claim 1, in which the EM source is a pinhole source.

3. A sensor as claimed in claim 1, in which the EM source, the baffle, first EM detector and second EM detector are arranged substantially in a straight line.

4. A sensor as claimed in claim 1, in which the sensor includes a cover of EM transmitting glass.

5. A sensor as claimed in claim 1, in which the infrared radiation source is an Infra Red LED and the detectors are photodiodes.

6. A sensor as claimed in claim 1, in which the distance between the EM source and the first sensor is between 0.1 cm and 0.6 cm.

7. A sensor as claimed in claim 1, in which the distance between the first sensor and the second sensor is between 0.1 cm and 1 cm.

8. An autoinjector comprising a liquid container, an injector, an injection contact portion, processor and a sensor adjacent the injection contact portion, the injector being arranged to inject liquid from the liquid container into a patient at the injection contact portion, the sensor being as described in claim 1 and the autoinjector being configured to use the injector to inject the liquid from the container into a subject only when a positive skin signal has been received from the sensor.

9. An autoinjector as claimed in claim 8, in which the autoinjector includes an ambient light sensor adjacent the sensor and the autoinjector is configured to activate the sensor only when the ambient light sensor detects ambient light levels below a threshold level.

10. A method of generating a signal indicative of contact of an object with skin, the object being equipped with a sensor on a contact portion thereof, the sensor comprising a processor, an EM source which projects a fine point of IR light, a baffle, a first EM detector and a second EM detector, the sensor arranged such that the EM source is located on a first side of the baffle and the first and second EM detectors are arranged on a second opposite side of the baffle at first and second distances from the EM source respectively, the first distance being less than the second distance, the method comprising the steps of:

a) using the processor to cause the source to emit EM radiation b) using the first and second EM detectors to generate first and second signals respectively, the signals being indicative of the intensity of EM radiation detected by the sensor; and c) using the processor to process the first and second signals wherein the processing comprises comparing the first signal against a first threshold, dividing the first signal by the second signal, and comparing the product to a second threshold, comparing a rate of change of each of said first and second signals to a third and a fourth threshold, and wherein a logic gate assesses the resultant signals to thereby generate a skin signal which is indicative of whether the sensor has detected skin and therefore whether the object has contacted skin.

* * * * *